United States Patent [19]

Blease

[11] Patent Number: 5,059,342

[45] Date of Patent: Oct. 22, 1991

[54] NOVEL CHEMICAL COMPOUNDS AND THEIR USE AS LOW FOAM SURFACTANTS AND ANTIFOAMING AGENTS

[75] Inventor: Trevor G. Blease, Guisborough, England

[73] Assignee: Imperical Chemical Industries PLC, London, England

[21] Appl. No.: 496,601

[22] Filed: Mar. 21, 1990

[51] Int. Cl.$^5$ .................. C11D 3/075; C11D 1/755; C09K 3/32; C07C 43/11

[52] U.S. Cl. ............... 252/174.21; 252/358; 568/613; 568/615

[58] Field of Search .......... 252/174.21, 358; 568/613, 618

[56] References Cited

U.S. PATENT DOCUMENTS

| | | | |
|---|---|---|---|
| 2,481,278 | 9/1949 | Ballard et al. | 568/613 |
| 2,626,243 | 1/1953 | Jacoby | 568/613 |
| 3,504,041 | 3/1970 | Weipert | 260/615 |
| 3,563,901 | 2/1971 | Crotty | 252/136 |
| 3,629,127 | 12/1971 | Palmer | 252/55 |
| 3,684,723 | 8/1972 | Best et al. | 252/358 |
| 4,364,777 | 12/1982 | Grünert et al. | 134/29 |
| 4,366,326 | 12/1982 | Vodraszka et al. | 252/174.22 |
| 4,405,490 | 9/1983 | Maas et al. | 252/358 |
| 4,548,729 | 10/1985 | Schmid et al. | 252/174.21 |
| 4,624,803 | 11/1986 | Balzer et al. | 252/527 |
| 4,780,237 | 10/1988 | Schmid et al. | 252/174.22 |
| 4,797,222 | 1/1989 | Hoefer et al. | 252/174.21 |
| 4,824,594 | 4/1989 | Hoeffkes et al. | 252/174.21 |
| 4,942,049 | 7/1990 | Schmid et al. | 426/329 |

*Primary Examiner*—Paul Lieberman
*Assistant Examiner*—Erin M. Higgins
*Attorney, Agent, or Firm*—Cushman, Darby & Cushman

[57] ABSTRACT

Novel chemical compounds which have formula $CH_3 CH_2 CH_2)(A)R$ in which (A) is a polyalkylene oxide chain comprising 5 to 18 alkylene oxide residues in which there are 0 to 10 propylene oxide residues for every 10 ethylene oxide residues and R is a $C_8$ to $C_{18}$ alkyl group are suitable for use as low foam surfactants or antifoaming agents in cleaning processes and rinsing applications.

10 Claims, No Drawings

NOVEL CHEMICAL COMPOUNDS AND THEIR USE AS LOW FOAM SURFACTANTS AND ANTIFOAMING AGENTS

This invention relates to novel chemical compounds and their use as low foam surfactants or antifoaming agents.

European Patent Specification 197434 claims the use of compounds of formula $$R^1\text{—}O(C_2H_4O)_nR^2$$

in which $R^1$ is a $C_8$ to $C_{18}$ alkyl group or alkenyl group, n is 7 to 16 and $R^2$ is a $C_4$ to $C_8$ alkyl group as low foam rinsing aids, and European Patent Specification 124815 discloses such compounds as components of low foam cleaning materials. It is however advantageous for incorporation into fully formulated compositions that the low foam surfactant or antifoaming agent is a liquid.

It is known from European Patent No 0036550 that compounds of formula $$ROA\text{—}CH(CH_3)_2$$

in which R is a $C_8$ to $C_{20}$ alkyl group and A is a polyalkylene glycol residue containing from 4 to 30 alkylene oxide units (of which 100–60 mol % are ethylene oxide units and from 0–40 mol % are propylene oxide or butylene oxide units or a mixture of these) are low foam alkali and acid stable surfactants.

In a subsequent patent to the same patentees and involving one of the same inventors (U.S. Pat. No. 4624803) it is disclosed that those surfactants, where they are ethylene oxide/propylene oxide copolymers, do not have an optimum action in practice, especially since they are not sufficiently biodegradable. The relatively complicated and expensive method of preparation is a disadvantage, preventing them from being used in industry. The solution proposed in U.S. Pat. No. 4,624,803 involved replacing the isopropyl group of the compound by a methyl, ethyl or allyl group, the methyl group being exemplified.

We have now surprisingly found that the aforesaid problem in compounds of the above general type may be dealt with satisfactorily by replacing the iso-propyl group by a normal propyl group and that the resultant products show attractive properties including low and/or antifoaming properties and are liquid at 20° C. providing that the polyalkylene glycol residue conforms to certain requirements This invention comprises novel chemical compounds (I) which are liquid at 20° C. which have a formula $$CH_3\ CH_2\ CH_2O\ (A)\ R \qquad (I)$$

in which (A) is a polyalkylene oxide chain which comprises 5 to 18 and preferably 8 to 14 and more preferably 9 to 12 alkylene oxide residues, preferably each residue having from 2 to 4 carbon atoms, in which there are from 0 to 10 and preferably from 1 to 8 and more preferably from 1 to 4 propylene oxide residues for every 10 ethylene oxide residues and R is a $C_8$ to $C_{18}$ and preferably $C_{12}$ to $C_{15}$ alkyl group. If (A) comprises propylene oxide residues they may be present as 1 one or more blocks, but (A) is suitably a random copolymer chain of ethylene oxide and propylene oxide residues.

The invention also comprises the use of compounds (I) as low foam surfactants or antifoaming agents in cleaning processes especially in the cleaning of hard surfaces for example, glass, metal, plastic and pottery including porcelain and china in dishwashing, and domestic or industrial washing for example, bottlewashing, metal degreasing, and tank cleaning/cleaning in place in the food and brewery industry and in rinsing.

The compounds (I) may also be used to control foam in for example sugar manufacture and fermentation processes, paper manufacture and in the textile industry as a wool scourer and a fibre lubricant.

The compounds (I) may be produced by reacting a compound of formula R(A)OH and/or an alkoxide thereof with a compound of formula $CH_3\ CH_2\ CH_2\ X$ in which X is a halogen for example, chlorine or bromine, in the presence of a base for example, an alkali metal hydroxide and/or carbonate thereby producing the compound (I), which may then be purified using standard techniques. The compound of formula R(A)OH may be produced by reacting an alcohol of formula ROH and/or an alkoxide thereof with at least one alkylene oxide to produce a compound of formula R(A)OH. Where more than one alkylene oxide is required in the compound (I), the alkylene oxides may be reacted with the alcohol and/or alkoxide either simultaneously, to produce a random copolymer, or sequentially, to produce a block copolymer.

The invention also comprises a process of cleaning a soiled hard surface by agitating the surface in an aqueous solution of a compound (I) or flowing a said solution over the soiled surface.

The invention also comprises a cleaning composition suitable on dilution with water for use in cleaning processes comprising a compound (I) an alkali and preferably a builder.

The above cleaning composition may also comprise a bleach, an anticorrosion agent and/or a solvent for example water.

Compound (I) is preferably present in an amount of 0.1 to 15% by weight, and more preferably 1 to 5% by weight of the said cleaning composition.

The alkali suitably comprises for example sodium or potassium hydroxide and/or carbonate, and may be present in a ratio of 10 to 500 and preferably 100 to 300 equivalents per mole of compound (I)

The builder may be a zeolite, but is preferably a water soluble builder for example nitrolotriacetic acid, or a condensed phosphate for example sodiumtripolyphosphate or tetrasodiumpyrophosphate, and may be present in a ratio of 0.01 to 1 and preferably 0.1 to 0.5 moles per mole of alkali.

The bleach may be an organic chlorine containing bleach for example trichloroisocyanuric acid, dichloroisocyanuric acid or preferably a salt of dichloroisocyanuric acid and preferably a sodium or potassium salt thereof, and is preferably employed in an amount of 1 to 5% and more preferably 2 to 3% by weight in the cleaning composition.

The anti-corrosion agent is suitably an alkali metal silicate, preferably sodium silicate and may be present in a ratio of 0.1 to 3 and preferably 0.2 to 1 mole per mole of alkali in the cleaning composition.

The cleaning composition is diluted with water for use advantageously in an amount of 0.5 to 10 g per liter of water and preferably 0.5 to 5 g per liter of water.

A suitable temperature range for cleaning process use is 50° to 100° C. and preferably 55° to 65° C.

The invention also comprises a process of rinsing a hard surface by agitating the surface in an aqueous solution of a compound (I) or flowing a said solution over the surface.

The invention also comprises a rinsing aid composition which may comprise water and which is suitable on dilution with water for use in rinsing which comprises a compound (I), preferably a water softening agent, and optionally a hydrotrope.

Compound (I) is preferably present in an amount of 5% to 45% and more preferably 5% to 35% by weight of the said aqueous rinsing aid composition.

The water softening agent suitably comprises for example condensed phosphates, citric acid, tartaric acid, glycolic acid, succinic acid and /or adipic acid and may be present in a ratio of 1 to 20 and preferably 2 to 10 moles per mole of compound (I) in the rinsing aid composition.

The hydrotrope is preferably isopropanol or an alkali metal aryl sulphonate, for example the sodium salt of cumene sulphonate or xylene sulphonate and may be present in a ratio of 0.1 to 50 and preferably 1 to 10 moles per mole of compound (I) in the rinsing aid composition.

The rinsing aid composition used advantageously in an amount of 0.1 to 1 5 g per liter of water and preferably 0.4 to 1.0 g per liter of water.

A suitable temperature for rinse aid use is 50° to 100° C. and preferably 65° to 85° C.

The invention also comprises an aqueous solution (AS) suitable on dilution with water for use in cleaning processes, especially in the cleaning of hard surfaces, and/or rinsing which comprises a compound (I), an acid, and optionally a hydrotrope.

Compound (I) is preferably present in an amount of 5% to 35% and preferably 10% to 25% by weight of the said aqueous solution (AS).

The acid suitably comprises for example phosphoric acid and/or phosphonic acid, and may be present in a ratio of 1 to 150 and preferably 5 to 100 equivalents per mole of compound (I).

The hydrotrope is preferably isopropanol, and may be present in a ratio of 0.1 to 50 and preferably 1 to 10 moles per mole of compound (I) in the aqueous solution (AS).

The aqueous solution (AS) as hereinbefore described is used advantageously in an amount of 0.1 to 5 g per liter of water and preferably 0.4 to 2 g per liter of water, at a temperature of 20° to 100° C. and preferably 55° to 85° C.

The invention is illustrated by the subsequent non limiting examples.

EXAMPLE 1

Production of Block form of Alkylpolyalkylene glycol of formula HO $(C_3H_6O)_3$ $(C_2H_4O)_9$ $C_{13/15}$)

$C_{13/15}$ oxoalcohol (10 kg) (where $C_{13/15}$ represents a ratio of 2:1 of $C_{13}$ and $C_{15}$ alkyl groups) and potassium hydroxide (0.076 kg) were reacted together in an autoclave, at a temperature of 125° to 130° C. To this reaction mixture ethylene oxide (19 kg) was added continuously over a period of 3 hours with continuous stirring whilst the temperature was maintained at 125° to 130° C. The reaction mixture was then stirred at a temperature of 125° C. to 130° C. for one further hour to allow substantially all of the ethylene oxide added to react.

Propylene oxide (8.5 kg) was then added continuously for a period of 2 hours to the reaction mixture with continuous stirring, the temperature was maintained at 120° to 125° C. This reaction mixture was then stirred at a temperature of 120° to 125° C. for a further 2 hours 30 minutes. The reaction mixture was then vacuum stripped at room temperature and 10 mm Hg, for 30 minutes and then at 110° C. to 120° C. and 10 mm Hg for a period of 1 hour 30 minutes.

This process yielded about 36 kg of block form of alkylpolyalkylene glycol of formula HO $(C_3H_6O)_3$ $(C_2H_4O)_9$ $C_{13/15}$.

EXAMPLE 2

Production of Random form of Alkylpolyalkylene glycol of formula HO $(C_3H_6O)_3$ $(C_2H_4O)_9$ $C_{13/15}$ $C_{13/15}$ oxoalcohol (10 kg) and potassium hydroxide (0.076 kg) were reacted together in an autoclave, at a temperature at 125° C. to 130° C. To this reaction mixture ethylene oxide (19 kg) and propylene oxide (8.5 kg) were added concurrently over a period of 5½ hours with continuous stirring, the temperature was maintained at 125° C. to 130° C. This reaction mixture was then stirred at a temperature of 125° C. to 130° C. for a further 2 hours. The reaction mixture was then vacuum stripped at room temperature and 10 mm Hg for 30 minutes and then at 110° C. to 120° C. and 10 mm Hg for a period of 1 hour 30 minutes.

This process yielded about 36 kg of random form of alkylpolyalkylene glycol of formula HO $(C_3H_6O)_3$ $(C_2H_4O)_9$ $C_{13/15}$.

EXAMPLE 3

Production of Block form of Alkylpolyalkylene glycol of formula HO $(C_3H_6O)_1$ $(C_2H_4O)_8 C_{13/15}$ The procedure of Example 1 was followed with the exceptions that the amounts of ethylene oxide and propylene oxide added were 22 kg and 3.8 kg respectively and the amount of $C_{13/15}$ oxoalcohol was 13kg.

This process yielded about 38 kg of block form of alkylpolyalkylene glycol of formula HO $(C_3H_6O)_1$ $(C_2H_4O)_8$ $C_{13/15}$.

EXAMPLE 4

Production of Random form of Alkylpolyalkylene glycol of formula HO $(C_3H_6O)_1$ $(C_2H_4O)_8$ $C_{13/15}$ The procedure of example 2 was followed with he exceptions that the amounts of ethylene oxide and propylene oxide added were 22 kg and 3.8kg respectively and the amount of $C_{13/15}$ oxoalcohol was 13 kg.

This process yielded about 38 kg of random form of alkylpolyalkylene glycol of formula HO $(C_3H_6O)_1$ $(C_2H_4O)_8$ $C_{13/15}$.

EXAMPLE 5

Production of Alkylpolyalkylene glycol ethers (Compound I) from Alkylpolyalkylene glycols obtained from Examples 1-4

Alkylpolyalkylene glycol obtained from example 1 or 2 (780g) or example 3 or 4 (620 g) was mixed with sodium hydroxide powder (240 g) and then 1-Bromopropane (246 g) was added continuously for a period of 1 hour under a nitrogen atmosphere, the temperature being maintained at approximately room temperature by use of an ice bath. The temperature of this reaction mixture was then raised to 120° C. and the reaction mixture was stirred for 4 hours. The reaction mixture was then quenched by pouring it into 400 g of water. The resultant organic and aqueous layers were then separated and the organic layer was washed with water two more times at a temperature of 90° C.

The alkylpolyalkylene glycol ether product was obtained by distillation at 100° C. and 100 millibar for 1 hour to remove 1-bromopropane, propan-1-ol and water to leave a residue of substantially pure alkylpolyalkylene glycol ether (compound (I)

EXAMPLE 6

TABLE 1

| Compound (I) | Product Characterisation Data | | |
|---|---|---|---|
| | Polymer Type | Turbidity* Point/°C. | Melting Point/°C.+ |
| (i) n $C_3H_7O(PO)_3(EO)_9$ R | Block | 43 | −11 |
| (ii) n $C_3H_7O(PO)_3(EO)_9$ R | Random | 46 | −16 |
| (iii) n $C_3H_7O(PO)_1(EO)_8$ R | Block | 44 | +3 |
| (iv) n $C_3H_7O(PO)_1(EO)_8$ R | Random | 46 | +10 | where
EO = Ethylene oxide unit
PO = Propylene oxide unit
R = A ratio of 2:1 of $C_{13}$ and $C_{15}$ alkyl groups
*Obtained according to British Standards Institute (BSI) 87/53362 (ISO 1065 - 1975 (E)) from a 10% w/w solution of compound (I) in an aqueous solution containing 25% butyl diglycol.
+Obtained according to method American Society for Testing and Materials (ASTM) D97-66.

EXAMPLE 7

Antifoaming Test Data

Data was obtained from a "chute et recyclage" apparatus as described in Association Francais de Normalisation (AFNOR) method NFT 73-412 involving the controlled circulation of a test solution, which consisted of a foaming solution and an antifoam solution, and the measurement of the resulting foam height.

The foaming solution used consisted of a 2–5% aqueous solution of the sodium salt of a $C_{12}$ alkyl benzene sulphonate. The antifoam solution used consisted of b 1% sodium hydroxide solution and 300 parts per million (ppm) compound (I) in 1 liter of demineralised water.

The antifoam solution was placed in the "chute et recyclage" apparatus and the solution heated to a temperature of 60° C. Foaming solution was then added, and the whole volume of solution was circulated at a rate of 50 liters per hour and the height of the resulting foam was recorded after 60 seconds. A series of experiments were performed in which the amount of foaming solution added was varied from 3 milliliters (ml) to 18 ml in 3 ml increments. A blank experiment containing no foaming solution was also carried out for each compound (I) tested.

A control experiment was carried out for comparative purposes in which the antifoam solution was replaced by 1% sodium hydroxide in 1 liter of demineralised water and no added compound (I). The results are given in Table 2.

TABLE 2

| | Millimeters of Foam formed after 60 seconds | | | | | | | |
|---|---|---|---|---|---|---|---|---|
| Compound (I) | 0 | 3 | 6 | 9 | 12 | 15 | 18 | (mls of foaming formulation added) |
| (i) n $C_3H_7O(PO)_3(EO)_9$ R (Block) | 0 | 7 | 12 | 70 | 290 | 450 | 450 | |
| (ii) n $C_3H_7O(PO)_3(EO)_9$ R (Random) | 0 | 6 | 18 | 70 | 340 | 445 | 470 | |
| (iii) n $C_3H_7O(PO)_1(EO)_8$ R (Block) | 0 | 3 | 15 | 105 | 155 | 420 | 475 | |
| (iv) n $C_3H_7O(PO)_1(EO)_8$ R (Random) | 0 | 4 | 7 | 10 | 250 | 375 | 450 | |
| (v) Water + NaOH | 17 | 65 | 250 | 320 | 425 | 470 | 480 | |

EXAMPLE 8

Antifoaming Test Data

Data was obtained from a "chute et recyclage" apparatus as described in Association Francais de Normalisation (AFNOR) method NFT 73-412 involving the controlled circulation of a test solution, which consisted of a foaming solution and an antifoam solution, and the measurement of the resulting foam height.

The foaming solution used consisted of 100 g of aqueous solution of 1.5% milk powder, 100 g of 1.5% sodium hydroxide solution, and 800 g of (soft) water. The antifoam solution used consisted of 30% of block n $C_3H_7O(PO)_3(EO)_9R$, 10% isopropanol, 5% citric acid and 55% demineralised water and was used in a concentration of 600 parts per million (ppm).

The whole volume of solution was circulated at a rate of 50 liters per hour and the height of the resulting foam was recorded after 3 minutes. A series of experiments were performed in which the temperature was held at 30° C., 50° C. and 70° C.

A control experiment was carried out for comparative purposes without any antifoam solution being present. The results are given in Table 3.

TABLE 3

| | Millimeters of Foam formed after 3 minutes | |
|---|---|---|
| Temperature (°C.) | Antifoam present | No antifoam present |
| 30 | 116 | >600 |
| 50 | 64 | >600 |
| 70 | 55 | >600 |

EXAMPLE 9

Dishwasher Test

No low foam surfactant present in the cleaning or rinsing process

A selection of crockery and cutlery which was soiled with various foods including baked beans, beetroot juice, custard, wine, tea and coffee was loaded into a "Miele G550" dishwasher. A powder detergent was used in the cleaning process which comprised, sodium silicate (13.5 g), pentasodium triphosphate (12.0 g), sodium carbonate (1.65 g), sodium sulphate (1.20 g) and sodium dichloroisocyanate (0.60 g) and the rinsing process used water only to rinse the crockery and cutlery. The dishwasher was operated according to its associated instructions and water was used at a temperature of 55° C. for the cleaning process and at a temperature of 70° C. for the rinsing process.

EXAMPLE 10

Dishwasher Test

Low foam surfactant present in the cleaning but not rinsing process

Example 9 was repeated with the exception that a low foam surfactant of formula n $C_3H_7O(PO)_3(EO)_9R$ (1.00 g) was added to the powder detergent to give an indication of the antifoaming effect and the detergent effect of the low foam surfactant. The rinsing process was conducted using water only as in Example 9.

EXAMPLE 11

Dishwasher Test

Low foam surfactant not present in the cleaning but present in the rinsing process Example 9 was repeated with the exception that a rinsing aid composition was used in the rinsing process which comprised 30% of block n $C_3H_7O(PO)_3(EO)_9R$, 10% isopropanol, 5% citric acid and 55% demineralised water and was used in a concentration of 600 parts per million (ppm) to give an indication of the antifoaming effect and the rinsing effect of the rinsing aid composition. The cleaning process was conducted using only the powder detergent as in Example 9 and no added low foam surfactant.

The results of Examples 9 to 11 were obtained by a qualitative visual examination of the various pieces of crockery and cutlery after they had been washed and rinsed in accordance with the above Examples. The relative amounts of foam produced in each Example were determined by qualitative observation of the rate of rotation of the rotor arm on the dishwasher during each Test (the rate of rotation of the rotor arm decreasing with an increase in the amount of foam produced during use). The results of Examples 9 to 11 are given in Table 4.

TABLE 4

| | Observations | | |
|---|---|---|---|
| Crockery | Example 9 | Example 10 | Example 11 |
| 6 dinner plates | All clean | All clean | All clean |
| 6 side plates | All clean | All clean | All clean |
| 6 bowls | All clean | All clean | All clean |
| 6 cups | 5 had sugar deposits on them | All clean | All clean |
| 6 saucers | All clean | All clean | All clean |
| 4 tumblers | All were marked | 2 slightly marked | All clean |
| 2 wine glasses | All were marked | All clean | All clean |
| 6 knives | 3 were marked | 2 were marked | All clean |
| 6 forks | 3 were marked | All clean | All clean |
| 6 spoons | All clean | All clean | All clean |

The amount of foam produced during Examples 10 (low foam surfactant present in the cleaning process) and 11 (low foam surfactant present in the rinsing process) was visibly less than that produced during Example 9 (low foam surfactant not present in the cleaning or rinsing process). Examples 10 and 11 illustrate that the addition of the low foam surfactant in the cleaning process and the rinsing process provides an improved detergency effect when compared with the results obtained without any low foam surfactant being present.

I claim:

1. Compounds of formula $$CH_3 CH_2 CH_2O (A) R$$

or mixtures thereof which are liquid at 20° C. in which (A) is a polyalkylene oxide chain which comprises 5 to 18 alkylene oxide residues in which there are from 1 to 8 propylene oxide residues for every 10 ethylene oxide residues and R is a $C_8$ to $C_{18}$ alkyl group.

2. Compounds as claimed in claim 1 in which (A) is a polyalkylene oxide chain which comprises 8 to 14 alkylene oxide residues and in which R is a $C_{12}$ to $C_{15}$ alkyl group.

3. Compounds as claimed in claim 1 in which (A) is a polyalkylene oxide chain which comprises ethylene oxide and propylene oxide residues only.

4. Compounds as claimed in claim 1 in which R is a $C_{12}$ to $C_{15}$ alkyl group.

5. Process of cleaning a soiled hard surface by agitating the surface in an aqueous solution of a compound as claimed in claim 1 or flowing a said solution over the soiled hard surface.

6. Process of rinsing a hard surface by agitating the surface in an aqueous solution of a compound as claimed in claim 1 or flowing a said solution over the cleaned surface.

7. Cleaning compositions suitable on dilution with water for use in a process of cleaning as claimed in claim 5 which comprises a compound as claimed in claim 1 and an alkali.

8. Rinsing aid compositions suitable on dilution with water for use in a process of rinsing as claimed in claim 6 which comprises a compound as claimed in claim 1 and a hydrotrope.

9. Aqueous solutions suitable on dilution with water for use in cleaning of hard surfaces and/or rinsing which comprises a compound as claimed in claim 1, an acid and optionally a hydrotrope.

10. A process in which a compound as claimed in claim 1 is produced by reacting a compound of formula HO (A) R with a compound of formula $CH_3 CH_2 CH_2 X$, in which X is a halogen, in the presence of a base.

* * * * *